United States Patent [19]

Roman

[11] 4,049,652

[45] Sept. 20, 1977

[54] ESTERS OF NITRO(TETRAHYDRO-2H-1,3-THIAZIN-2-YLIDENE)ACETIC ACID

[75] Inventor: Steven A. Roman, Oakdale, Calif.

[73] Assignee: Shell Oil Company, Houston, Tex.

[21] Appl. No.: 706,311

[22] Filed: July 19, 1976

[51] Int. Cl.² .......................................... C07D 279/06
[52] U.S. Cl. ..................................... 544/54; 544/55; 424/246

[58] Field of Search ..................................... 260/243 R

[56] References Cited

U.S. PATENT DOCUMENTS 3,993,648  11/1976  Powell .................................. 260/243

Primary Examiner—John M. Ford

[57] ABSTRACT

Novel insecticidal esters of nitro(tetrahydro-2H-1,3-thiazin-2-ylidene)acetic acid.

2 Claims, No Drawings

ESTERS OF NITRO(TETRAHYDRO-2H-1,3-THIAZIN-2-YLIDENE)ACETIC ACID

DESCRIPTION OF THE INVENTION

It has been found that useful insecticdial activity is possessed by certain 1,3-benzodioxol-5-ylmethyl esters of nitro(tetrahydro-'H-1,3-thiazin-2-ylidene)acetic acid. These esters are resonance hybrids, the principal forms contributing thereto being described by the formulae (A)

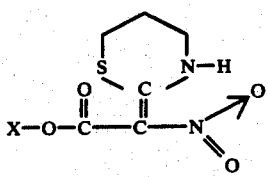

(B)

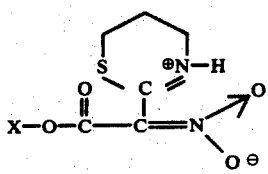

wherein X represents the 1,3-benzodioxol-5-ylmethyl moiety, having the formula

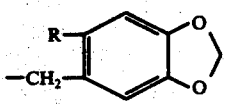

wherein R is hydrogen, middle halogen (i.e., bromine or chlorine), cyano, nitro or alkyl of from one to three carbon atoms.

These compounds also can exist in the corresponding tautomeric enol form which can be described by the formula (C)

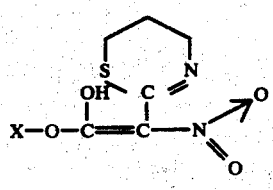

The resonance hybrid may exist as either of two geometric (cis-trans) isomers, depending upon the spatial relationship of the moieties about the bond between the carbon atom of the nitromethylene moiety and the ring carbon atom to which it is joined.

The enol form (Form C) can be designated as a 1X-O-2-nitro-2-(5,6-dihydro-4H-1,3-thiazin-2-yl)vinyl alcohol. The left-hand form of the resonance hybrid (Form A) can be designated as an ester of nitro (tetrahydro-2H-1,3-thiazin-2-ylidene)acetic acid. The right-hand form (Form B) can be designated as an 2-(X-oxycarbonyl-aci-nitromethyl)-5,6-dihydro-4H-1,3-thiazinium hydroxide inner salt.

In this specification, for the sake of simplicity, these compounds will be referred to generally as the 1,3-benzodioxol-5-ylmethyl esters of nitro(tetrahydro-2H-1,3-thiazin-2-ylidene)acetic acid. This terminology is intended to include all of the contributors to the resonance hybrids, the geometric isomers and the enol forms, as well as mixtures thereof.

For illustration, preparation of a typical species ester of the genus is described in the example included hereinafter. Other typical illustrative species of this genus of esters include those wherein the symbol R represents the following moieties, this manner of naming these species being accurate, yet pointing out the differences between the different species more clearly than if the entire, complicated name of each species were to be given:

R bromine
chlorine
nitro
cyano
isopropyl

Compounds of this invention can be prepared by the base-promoted transesterification of an alkyl ester of nitro(tetrahydro-2H-1,3-thiazine-2-ylidene)acetic acid (X = alkyl, for example, methyl or ethyl) which can be prepared by zinc ion-catalyzed reaction of 5,6-dihydro-2-(methylthio)-4H-1,3-thiazine (A. F. McKay et al., J. Am. Chem. Soc. 80, 3339 (1950)) with an alkyl nitroacetate (S. Zen, et al. Kogyo Kagaku Zasshi, 74, 70 (1971)).

The ester interchange follows the conventional catalyzed reaction of an ester with the alcoholate of the appropriate piperonyl alcohol. The interchange can be effected by treating the appropriate alcohol in solvent such as tetrahydrofuran or dimethylformamide with an alkali metal hydride, then adding the ester, also in the solvent. The reaction of the alcohol and hydride usually is exothermic so that cooling is usually needed to control the temperature of the reaction mixture to 0–10° C. Reaction of the alcoholate with the ester ordinarily can be conducted at room temperature.

Recovery of the product is most effectively attained in most cases by quenching the final reaction mixture in water, treating the aqueous mixture with a suitable solvent such as ether and/or methylene chloride, to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ether.

These procedures for preparing compounds of this invention are illustrated in the following example of the preparation of a particular species of such compounds. The identity of the product and of the precursor intermediate employed was confirmed by appropriate elemental and spectral analyses.

EXAMPLE 1

1,3-benzodioxol-5-ylmethyl nitro(tetrahydro-2H-1,3-thiazin-2-ylidene)acetate (1)

To a mixture of 221 g of 5,6-dihydro-2-(methylthio)-4H-1,3-thiazine (A. F. McKay et al., J. Am. Chem. Soc., 80, 3339 (1950)) and 1 g of zinc chloride at about 100°, 202 g of methyl nitroacetate (S. Zen et al., Kogyo Kagaku Zasshi, 74, 70 (1971)) was added dropwise over a 30-minute period. The resulting mixture was heated for 4 hours at 95–105°. 200 ml of isopropyl alcohol then was added to the hot mixture, then 400 ml of ether was added. The resulting mixture was filtered to give methyl nitro (tetrahydro-2H-1,3-thiazin-2-ylidene)- acetate (1A), as a pale yellow solid, m.p.: 107°–108° C.

A solution of 50 g of piperonyl alcohol in 100 ml of dimethylformamide (DMF) was slowly added dropwise to a stirred mixture of 3.8 g of sodium hydride in 50 ml of DMF at 5°. The resulting mixture was allowed to warm to room temperature and stirred until no more gas evolved. Then 8.7 g of 1A was added and the mixture was stirred overnight at room temperature. The mixture was poured into ice water and was extracted with ether and then with a 50:50 by volume mixture of methylene chloride and ether. The aqueous phase was separated and acidified with acetic acid to precipitate a solid that was collected and recrystallized from ethanol to give 1, as a yellow solid, m.p.: 129°–129°.

The compounds of this invention are of particular interest for control of the larvae ("caterpillar" or "worm" forms) of insects of the genus Heliothis, such as *H. zea* (corn earworm, cotton bollworm, tomato fruitworm), *H. virescens* (tobacco budworm). In tests that have been conducted with Compound 1, it has exhibited very high activity with respect to larvae of the corn earworm, some activity with respect to the houseflies and low, or no, toxicity to the pea aphids, 2-spotted spider mites and mosquito larvae.

Activity of Compound 1 with respect to insects was determined by establishing the $LD_{50}$ dosage (in milligrams of test compound per 100 milliliters of solvent required in the solution of suspension of test compound used as a spray) to kill 50% of the test insects. The test insects were the housefly, corn earworm, pea aphid and 2-spotted spider mite. Activity with respect to mosquito larvae was determined by placing the larvae in water containing the test compound.

The invention includes within its scope insecticidal compositions comprising an adjuvant — that is, a carrier, optionally a surface-active agent — and, as active ingredient, the insecticide of this invention. Likewise the invention includes also a method of combatting insect pests at a locus which comprises applying to the locus an effective amount of the insecticide of the invention.

The term "carrier" as used herein means a material, which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight mono-, di- and trialkylamines; condensates of these with ethylene oxide and/or propylene oxide; condensation products of fatty alcohols or alkyl phenols for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of a dispersing agent and, where necessary, up to 10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of the toxicant of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my invention:

1. A resonance hybrid in which the significant forms are represented by the formulae

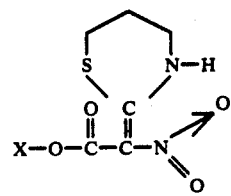

and

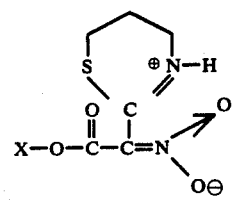

and the enol form represented by the formula

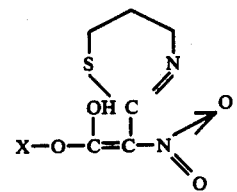

wherein X represents the moiety

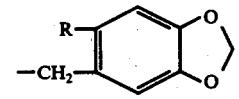

wherein R represents hydrogen, middle halogen, cyano, nitro or alkyl of from one to three carbon atoms.

2. A hybrid according to claim 1 wherein R is hydrogen.

* * * * *